(12) United States Patent
Ochi et al.

(10) Patent No.: US 10,603,395 B2
(45) Date of Patent: Mar. 31, 2020

(54) FLUID STERILIZATION DEVICE

(71) Applicant: Nikkiso Co., Ltd, Tokyo (JP)

(72) Inventors: Tetsumi Ochi, Hakusan (JP); Shinya Watanabe, Hakusan (JP)

(73) Assignee: NIKKISO CO., LTD., Shibuya-Ku, Tokyo (JP)

( * ) Notice: Subject to any disclaimer, the term of this patent is extended or adjusted under 35 U.S.C. 154(b) by 0 days.

(21) Appl. No.: 16/279,376

(22) Filed: Feb. 19, 2019

(65) Prior Publication Data

US 2019/0175771 A1    Jun. 13, 2019

Related U.S. Application Data

(63) Continuation of application No. PCT/JP2017/029114, filed on Aug. 10, 2017.

(30) Foreign Application Priority Data

Aug. 23, 2016   (JP) .................................. 2016-163130

(51) Int. Cl.
*A61L 2/10*      (2006.01)
*C02F 1/32*      (2006.01)

(52) U.S. Cl.
CPC    *A61L 2/10* (2013.01); *C02F 1/32* (2013.01); *C02F 1/325* (2013.01);
(Continued)

(58) Field of Classification Search
CPC .... A61L 2/10; A61L 2202/11; A61L 2202/14; C02F 1/32; C02F 1/35
See application file for complete search history.

(56) References Cited

U.S. PATENT DOCUMENTS 6,514,405 B1    2/2003   Lifschitz
2003/0075490 A1  4/2003   Lifschitz
(Continued)

FOREIGN PATENT DOCUMENTS

JP    201183295 A    9/2011
JP    2013034979 A   2/2013
(Continued)

OTHER PUBLICATIONS

Machine translation of JP,2013-034979,A Feb. 21, 2013.*
(Continued)

*Primary Examiner* — Nicole M Ippolito
*Assistant Examiner* — Sean M Luck
(74) *Attorney, Agent, or Firm* — Muncy, Geissler, Olds & Lowe, PC

(57) ABSTRACT

A fluid sterilization device includes: a straight tube that defines a processing flow passage; a light source that radiates ultraviolet light toward the processing flow passage in an axial direction of the straight tube; and a light receiving part that receives a portion of the ultraviolet light output from the light source. The straight tube is made of a fluororesin. The straight tube includes a recess formed in a part of an outer wall surface of the straight tube such that a thin part is partly provided in the straight tube. The thin part has a radial thickness from an inner wall surface of the straight tube that is smaller than a thickness in other parts. The light receiving part is provided in the recess to receive the ultraviolet light transmitted through the thin part.

9 Claims, 1 Drawing Sheet

(52) U.S. Cl.
CPC ........ *A61L 2202/11* (2013.01); *A61L 2202/14* (2013.01); *C02F 2201/326* (2013.01); *C02F 2201/3222* (2013.01); *C02F 2303/04* (2013.01)

(56) References Cited

U.S. PATENT DOCUMENTS

| | | | | |
|---|---|---|---|---|
| 2003/0205454 | A1* | 11/2003 | Hlavinka | A61K 41/0019 204/157.15 |
| 2005/0220665 | A1* | 10/2005 | Ding | A61B 1/123 422/20 |
| 2006/0144700 | A1* | 7/2006 | Carson | A61L 2/035 204/252 |
| 2007/0272877 | A1* | 11/2007 | Tribelsky | A61L 2/10 250/431 |
| 2009/0230059 | A1* | 9/2009 | McGuire | C02F 9/00 210/638 |
| 2010/0061885 | A1* | 3/2010 | Harley | G01N 21/85 422/3 |
| 2010/0237254 | A1* | 9/2010 | Mason | A61L 2/10 250/435 |
| 2011/0212185 | A1* | 9/2011 | Tanaka | A01G 7/00 424/600 |
| 2012/0051977 | A1* | 3/2012 | Boodaghians | C02F 1/325 422/117 |
| 2013/0236353 | A1 | 9/2013 | Blechschmidt et al. | |
| 2016/0083272 | A1 | 3/2016 | Rajagopalan et al. | |
| 2016/0207795 | A1 | 7/2016 | Hanada | |

FOREIGN PATENT DOCUMENTS

| | | |
|---|---|---|
| JP | 2013056159 A | 3/2013 |
| JP | 2016523594 A | 8/2016 |
| WO | WO2015046014 A1 | 4/2015 |

OTHER PUBLICATIONS

International Preliminary Report on Patentability with English Translation, dated Aug. 10, 2017, in International Application No. PCT/CN2017/029114.

International Search Report and Written Opinion dated Aug. 10, 2017, in International Application No. PCT/CN2017/029114.

Office Action dated Nov. 26, 2019 issued in corresponding Japanese Application No. 2016-163130 (with English translation).

* cited by examiner

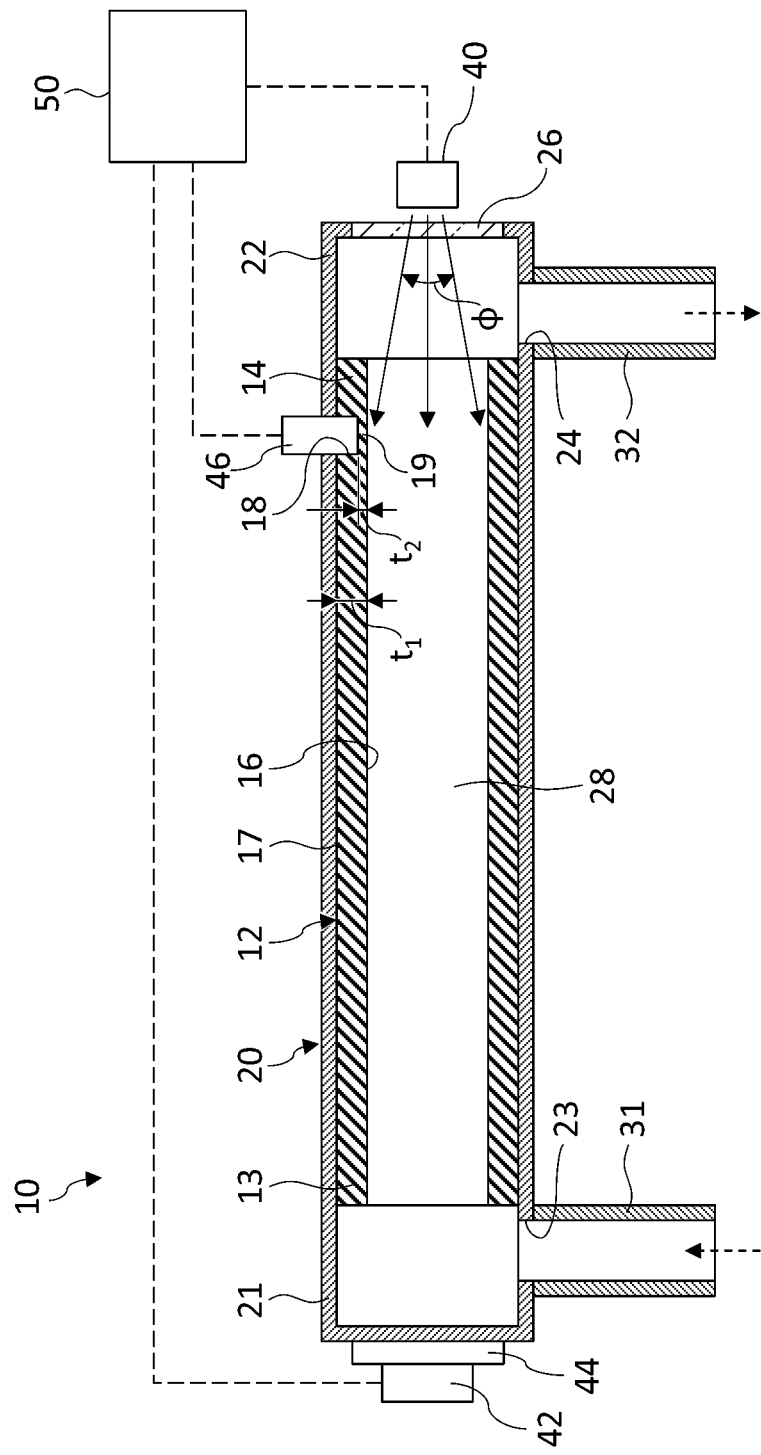

FLUID STERILIZATION DEVICE

RELATED APPLICATION

Priority is claimed to Japanese Patent Application No. 2016-163130, filed on Aug. 23, 2016, the entire content of which is incorporated herein by reference.

BACKGROUND OF THE INVENTION

1. Field of the Invention

The present invention relates to fluid sterilization devices and, more particularly, to a technology of sterilizing a fluid by irradiating the fluid with ultraviolet light.

2. Description of the Related Art

It is known that ultraviolet light has sterilization capability. Devices that radiate ultraviolet light are used for sterilization in medical and food processing fronts. Devices that sterilize a fluid such as water continuously by irradiating the fluid with ultraviolet light are also used. One example of such a device is an ultraviolet irradiation device in which a straight ultraviolet lamp and a cylindrical lamp sleeve are provided in a processing tank and water in the processing tank subject to treatment is irradiated with ultraviolet light. The illuminance of the ultraviolet lamp is measured by using an ultraviolet monitor, and a transparent window made of quartz glass etc. is provided between the ultraviolet monitor and the ultraviolet lamp.

The amount of light measured by the ultraviolet monitor is affected by factors such as the ultraviolet transmittance of the fluid in the processing tank, reduction in the transmittance due to attachment of stain on the transparent window in front of the monitor, etc., which could make it difficult to measure the light intensity of the light source itself properly.

SUMMARY OF THE INVENTION

In this background, one illustrative purpose of the present invention is to provide a fluid sterilization device in which the accuracy of monitoring a light source is increased.

A fluid sterilization device according to an embodiment includes: a straight tube that defines a processing flow passage; a light source that radiates ultraviolet light toward the processing flow passage in an axial direction of the straight tube; and a light receiving part that receives a portion of the ultraviolet light output from the light source. The straight tube is made of a fluororesin. The straight tube includes a recess formed in a part of an outer wall surface of the straight tube such that a thin part is partly provided in the straight tube. The thin part has a radial thickness from an inner wall surface of the straight tube that is smaller than a thickness in other parts. The light receiving part is provided in the recess to receive the ultraviolet light transmitted through the thin part.

According to this embodiment, a light receiving part is provided at the side of the processing flow passage in a configuration in which ultraviolet light is radiated in the axial direction in the processing flow passage, so as to make it possible to detect the amount of ultraviolet light from the light source. By providing a thin part made of fluororesin in front of a detector, the thin part can be used as a transparent window for transmitting ultraviolet light. Because the stain is not easily attached to a fluororesin than a glass material, the feature makes the thin part embodying the transparent window less easily stained. Further, by scattering or diffusing a portion of the ultraviolet light incident on the inner wall surface of the processing flow passage at a high angle of incidence, the direction of travel of a portion of transmitted ultraviolet light can be changed and the transmitted ultraviolet light can be guided toward the light receiving part. This increases the percentage of the amount of ultraviolet light incident on the light receiving part and increases the accuracy of monitoring the light source.

The light source may be provided to radiate the ultraviolet light from a first end to a second end of the straight tube, and the recess may be provided at a position nearer the first end than the second end.

The first end may be positioned downstream in the processing flow passage, and the second end may be positioned upstream in the processing flow passage.

The recess may be provided at a position where the ultraviolet light from the light source is adapted to be directly incident.

The fluid sterilization device may further include a window member that partitions between the light source and the processing flow passage; and a vibrator that vibrates the window member.

The fluid sterilization device may further include a controller that operates the vibrator based on an amount of ultraviolet light incident on the light receiving part.

The fluid sterilization device may further include a controller that controls an output of the light source based on an amount of ultraviolet light incident on the light receiving part.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

The sole FIGURE is a cross-sectional view schematically showing a configuration of a fluid sterilization device according to an embodiment.

DETAILED DESCRIPTION OF THE INVENTION

The invention will now be described by reference to the preferred embodiments. This does not intend to limit the scope of the present invention, but to exemplify the invention.

A detailed description will be given of embodiments of the present invention with reference to the drawings. Like numerals are used in the description to denote like elements and a duplicate description is omitted as appropriate.

The sole FIGURE schematically shows a configuration of a fluid sterilization device 10 according to an embodiment. The fluid sterilization device 10 includes a straight tube 12, a housing 20, an inflow tube 31, an outflow tube 32, a light source 40, a vibrator 42, a vibration plate 44, a light receiving part 46, and a controller 50. The fluid sterilization device 10 is used to irradiate a fluid flowing in a processing flow passage 28 defined by the straight tube 12 with ultraviolet light so as to sterilize the fluid.

The housing 20 includes an inflow end 21, an outflow end 22, an inflow port 23, an outflow port 24, and a window member 26. The housing 20 extends from the inflow end 21 to the outflow end 22 in the axial direction and houses the straight tube 12 inside. The vibrator 42 is fitted to the inflow end 21 via the vibration plate 44. The window member 26 for transmitting the ultraviolet light from the light source 40 is provided at the outflow end 22. The window member 26 is made of a material having a high ultraviolet transmittance such as quartz (SiO2), sapphire (Al2O3), and amorphous fluororesin.

The inflow port 23 is provided in the vicinity of the inflow end 21. The inflow tube 31 extending in a direction intersecting or orthogonal to the axial direction of the housing 20 is fitted to the inflow port 23. The outflow port 24 is provided in the vicinity of the outflow end 22. The outflow tube 32 extending in a direction intersecting or orthogonal to the axial direction of the housing 20 is fitted to the outflow port 24.

The straight tube 12 includes an upstream end 13, a downstream end 14, an inner wall surface 16, and an outer wall surface 17, and a recess 18. The straight tube 12 extends from the upstream end 13 to the downstream end 14 in the axial direction and has, for example, a length three times as large as the inner diameter or more. The straight tube 12 is a liner coating the inner surface of the housing 20. The straight tube 12 is housed inside the housing 20 at a position between the inflow port 23 and the outflow port 24 and defines the processing flow passage 28. The the straight tube 12 is provided such that the upstream end 13 is positioned in the vicinity of the inflow port 23, and the downstream end 14 is positioned in the vicinity of the outflow port 24.

The straight tube 12 is made of a fluororesin material and is, for example, made of polytetrafluoroethylene (PTFE), which is a fully fluorinated resin. PTFE is a chemically stable material having excellent durability, heat resistance, and chemical resistance. PTFE also has a high ultraviolet reflectivity. Therefore, by providing the straight tube 12 made of PTFE, the ultraviolet light from the light source 40 can be reflected by the inner wall surface 16 to propagate in the axial direction of the straight tube 12.

The straight tube 12 is formed to have a uniform thickness between the inner wall surface 16 and the outer wall surface 17 except in the recess 18. The thickness t1 of the straight tube 12 is 3 mm or larger, and, preferably, 5 mm or larger. By configuring the straight tube 12 to have a certain thickness t1 or larger, the reflectivity of ultraviolet light incident on the inner wall surface 16 is increased. Our knowledge shows that, when the straight tube 12 is made of PTFE, the diffuse reflectivity of ultraviolet light is ensured to be about 90% or higher by configuring the thickness t1 of the straight tube 12 to be 3 mm or larger.

The recess 18 is formed in a part of the outer wall surface 17 of the straight tube 12. The recess 18 is provided for mounting of the light receiving part 46 and is configured to embody a thin part 19 having a radial thickness t2 from the inner wall surface 16 smaller than the thickness t1 of the other parts. The thickness t2 of the thin part 19 is formed to be small enough to ensure that a portion of the ultraviolet light from the light source 40 is transmitted through the thin part 19 and is large enough to maintain the mechanical strength. The thickness of the thin part 19 is, for example, not less than 0.2 mm and not more than 2.0 mm, and, preferably, not less than 0.5 mm and not more than 1.0 mm. Our knowledge shows that, when the straight tube 12 is made of PTFE, the diffuse transmittance of ultraviolet light will be about 5%~10% when the thickness t2 of the thin part 19 is 2.0 mm, and that the diffuse transmittance of ultraviolet light will be about 10%~15% when the thickness t2 is 1.0 mm. By providing the thin part 19 of the thickness t2 like this, a portion of the ultraviolet light incident on the thin part 19 is caused to be transmitted so that a portion of the ultraviolet light is caused to be incident on the light receiving part 46.

It is preferred that the recess 18 be provided at a position nearer the downstream end 14 than the upstream end 13 and provided at a position near the light source 40. As illustrated in the FIGURE, for example, the recess 18 is provided at a position in the vicinity of the downstream end 14 and at a position where the ultraviolet light from the light source 40 is directly incident. By providing the recess 18 near the light source 40, the amount of attenuation of the intensity of ultraviolet light incident on the light receiving part 46 in the presence of the fluid flowing in the processing flow passage 28 is reduced.

The light source 40 is a so-called ultra violet-light emitting diode (UV-LED) that includes a light emitting device configured to emit ultraviolet light. It is preferred that the central wavelength or peak wavelength of the light emitting device included in the light source be included in a range of about 200 nm-350 nm and that the light emitting device emit ultraviolet light near 260 nm~270 nm having a high sterilizing efficiency. Such an ultraviolet LED is exemplified by an aluminum gallium nitride (AlGaN) based LED.

The light source 40 is provided in the vicinity of the window member 26 and is arranged to radiate ultraviolet light in the processing flow passage 28 in the axial direction via the window member 26. The light source 40 may include an adjustment mechanism for adjusting the angle of light distribution of the light emitting device. In the case the directivity angle or orientation angle of the light emitting device included in the light source 40 is 60° or larger, 90° or larger, or 120° or larger, for example, the adjustment mechanism adjusts the output angle so that the angle of light distribution $\varphi$ is 30° or smaller. The adjustment mechanism may be comprised of a transmission type optical system such as a lens or comprised of a reflection type optical system such as a concave mirror.

The adjustment mechanism ensures that the majority of the ultraviolet light output from the light source 40 enters the straight tube 12 by adjusting the angle of light distribution $\varphi$. The adjustment mechanism may configure the angle of incidence of the ultraviolet light on the inner wall surface 16 of the processing flow passage 28 to be 75° or larger. Our knowledge shows that, in the case the inner wall surface 16 is made of PTFE, the reflectivity on the surface will be extremely high if the angle of incidence on PTFE is is 70° or larger. For this reason, it is ensured that a high-intensity ultraviolet light can propagate a long distance in the processing flow passage 28, by adjusting the angle of ultraviolet light distribution by using the adjustment mechanism.

The vibrator 42 is, for example, an ultrasonic vibrator that gives the housing 20 vibration to help remove the stain attached to the inner surface of the housing 20 or the inner surface of the window member 26. The vibrator 42 is fitted to the inflow end 21 of the housing 20 via, for example, the vibration plate 44. The vibrator 42 is operated in accordance with a command from the controller 50. The vibrator 42 is operated intermittently, i.e., at predetermined time periods like 30 minutes and 1 hour to remove the stain attached to the inner surface of the housing 20 or the window member 26.

The light receiving part 46 receives a portion of the ultraviolet light output from the light source 40 and transmits information on the amount of ultraviolet light received to the controller 50. The light receiving part 46 includes a light amount sensor such as a photodiode. The light amount sensor included in the light receiving part 46 may be provided in the recess 18 or outside the housing 20. In the latter case, one end of an optical fiber may be inserted into the recess 18 so that the ultraviolet light output from the other end of the optical fiber is incident on the light amount sensor.

The controller 50 operates the light source 40 and the vibrator 42 based on light amount information from the light receiving part 46. The controller 50 may operate the vibrator 42 to remove the stain attached to the inner surface of the window member 26 when the light amount information acquired indicates a light amount below a predetermined threshold value. The controller 50 may operate the light source 40 to increase the output intensity of the light source 40 when the light amount information acquired after the vibrator 42 is operated continues to indicate a value below the predetermined threshold value. The controller 50 may output alert information indicating that the desired sterilization effect cannot be obtained when the light amount information acquired after the light source 40 is operated to increase the output intensity continues to indicate a value below the predetermined threshold value.

With the above-described configuration, the fluid sterilization device 10 irradiates the fluid flowing in the processing flow passage 28 with the ultraviolet light from the light source 40. The amount of ultraviolet light output from the light source 40 is detected by the light receiving part 46 and is transmitted to the controller 50. Thus, it is possible, according to the embodiment, to sterilize the fluid while monitoring the output intensity of the light source 40. The controller 50 causes the fluid flowing in the processing flow passage 28 to be irradiated with ultraviolet light of an intensity sufficient for sterilization, by operating the vibrator 42 or changing the condition of driving the light source 40 when the amount of ultraviolet light drops. This prevents the ultraviolet irradiation level from becoming insufficient due to the stain inside the housing 20 or degradation of the light source 40 and prevents the fluid not sufficiently sterilized from flowing out. In this way, a highly reliable fluid sterilization device 10 is provided.

According to the embodiment, the inner wall surface 16 is made of a fluororesin, which is hydrophobic. Therefore, the stain is not easily attached to the inner wall surface 16. Consequently, it is easy to maintain the processing flow passage 28 in a sanitized condition. Further, since the stain is not easily attached to the surface of the thin part 19 embodying the transparent window of the light receiving part 46, the amount of light detected is prevented from being lowered due to the stain on the transparent window. If a glass material such as quartz is used in the transparent window of the light receiving part 46, the stain is easily attached because glass is hydrophilic. Therefore, the stain may be accumulated on the transparent window with use and may make it impossible to measure the amount of ultraviolet light accurately. Meanwhile, the transparent window of the light receiving part 46 according to the embodiment is made of a fluororesin such as PTFE so that attachment of the stain is suitably prevented and the measurement accuracy is prevented from being lowered due to the accumulation of the stain.

According to the embodiment, light amount detection not affected so much by the ultraviolet transmittance of the fluid flowing in the processing flow passage 28 is realized by providing the light receiving part 46 at a position near the light source 40. In the case of a configuration in which ultraviolet light is radiated in the axial direction in the straight tube 12, the light receiving part may be provided at an end opposite to the light source 40 (the upstream end 13 or the inflow end 21). In this case, the distance from the light source 40 to the light receiving part 46 may be long depending on the length of the processing flow passage 28. The amount of light detected may vary significantly in accordance with the ultraviolet transmittance of the fluid flowing in the processing flow passage 28. Meanwhile, according to the embodiment, the light receiving part 46 can be located in the vicinity of the light source 40 by providing the light receiving part 46 at the side of the straight tube 12. This reduces the variation in the amount of light detected in accordance with the ultraviolet transmittance of the fluid and makes it possible to measure the output intensity of the light source 40 more accurately.

According to the embodiment, the ultraviolet light incident on the thin part 19 is scattered and diffused and is caused to be incident on the light receiving part 46, by using a fluororesin in the thin part 19 that embodies the transparent window of the light receiving part 46. If a transparent glass material is used in the transparent window of the light receiving part 46, it may not be possible to guide the ultraviolet light incident on the glass window at a high angle of incident to the light receiving part 46 properly. Also, the proportion of components reflected on the surface of the glass window may amount to a considerable percentage. In particular, the angle of light distribution $\varphi$ of the light source 40 is configured to be small (e.g., 30° or smaller) in this embodiment. Therefore, the majority of ultraviolet light is incident on the thin part 19 at a large angle of incidence (e.g., 75° or larger). In this embodiment, the thin part 19 is made of a fluororesin so that the the ultraviolet light incident on the thin part 19 is not linearly transmitted through the thin part 19 but is repeatedly scattered and diffused inside the resin and is diffusely transmitted accordingly. As a result, a portion of the ultraviolet light transmitted through the thin part 19 will change the direction of travel and travel toward the light receiving part 46 accordingly. As a result, it is ensured that a larger amount of ultraviolet light is incident on the light receiving part 46 even if the light receiving part 46 is provided at the side of the straight tube 12 in a configuration in which ultraviolet light is radiated in the axial direction.

Described above is an explanation based on an exemplary embodiment. The embodiment is intended to be illustrative only and it will be understood by those skilled in the art that various design changes are possible and various modifications are possible and that such modifications are also within the scope of the present invention.

In the embodiment described above, the vibrator 42 is provided at the inflow end 21 and the light source 40 is provided at the outflow end 22. In one variation, the arrangement of the vibrator 42 and the light source 40 may be reversed, and the light source and the window member may be provided at the inflow end 21 and the vibrator may be provided at the outflow end 22. In this case, the recess in which the light receiving part is provided may be provided in the vicinity of the upstream end 13. In other words, the recess in which the light receiving part is provided may be provided in the vicinity of the light source.

In a further variation, the light source may be provided both at the inflow end 21 and the outflow end 22. In this case, the recess may be provided in the vicinity of both the upstream end 13 and the downstream end 14, and the light receiving part may be provided in the respective recesses. In the case of this variation, the vibrator may be provided at the side of the housing 20.

The fluid sterilization device according to the embodiments and variations described above is described as a device for irradiating a fluid such water with ultraviolet light so as to sterilize the fluid. In one variation, the inventive sterilization device may be used for a purification process that decomposes organic substance included in a fluid by using ultraviolet irradiation.

It should be understood that the invention is not limited to the above-described embodiment but may be modified into various forms on the basis of the spirit of the invention. Additionally, the modifications are included in the scope of the invention.

What is claimed is:

1. A fluid sterilization device comprising:
   a straight tube that defines a processing flow passage, wherein the straight tube is made of polytetrafluoroethylene (PTFE), the straight tube comprises a recess formed in a part of an outer wall surface of the straight tube such that a thin part is partly provided in the straight tube, and the thin part has a radial thickness from an inner wall surface of the straight tube that is smaller than a radial thickness of the straight tube other than the thin part;
   a light source that radiates ultraviolet light toward the processing flow passage in an axial direction of the straight tube; and
   a light receiving part
   provided in the recess to receive the ultraviolet light transmitted through the thin part.

2. The fluid sterilization device according to claim 1, wherein
   the light source is provided to radiate the ultraviolet light from a first end to a second end of the straight tube, and
   the recess is provided at a position nearer the first end than the second end.

3. The fluid sterilization device according to claim 2, wherein
   the first end is positioned downstream in the processing flow passage, and the second end is positioned upstream in the processing flow passage.

4. The fluid sterilization device according to claim 1, further comprising:
   a window member that partitions between the light source and the processing flow passage; and
   a vibrator that vibrates the window member.

5. The fluid sterilization device according to claim 4, further comprising:
   a controller that operates the vibrator based on the ultraviolet light incident on the light receiving part.

6. The fluid sterilization device according to claim 1, further comprising:
   a controller that controls an output of the light source based on the ultraviolet light incident on the light receiving part.

7. The fluid sterilization device according to claim 1, wherein
   the light receiving part detects the ultraviolet light output from the light source incident on the light receiving part.

8. The fluid sterilization device according to claim 1, wherein
   the light receiving part receives and detects the ultraviolet light transmitted outward from an interior of the processing flow passage and through the thin part.

9. The fluid sterilization device according to claim 1, wherein
   the radial thickness of the thin part of the straight tube is 2 mm or smaller, and the radial thickness of the straight tube other than the thin part is 3 mm or larger.

* * * * *